(12) United States Patent
Zheng et al.

(10) Patent No.: US 6,863,670 B2
(45) Date of Patent: Mar. 8, 2005

(54) HIGH EFFICIENCY EXTERNAL COUNTERPULSATION APPARATUS AND METHOD FOR CONTROLLING SAME

(75) Inventors: Zhensheng Zheng, Guangzhou (CN); Zhili Huang, Guangzhou (CN); Ziqiang Huang, Xiantan (CN); Shifang Yang, Guangzhou (CN); Ying Liao, Guangzhou (CN)

(73) Assignee: Vasomedical, Inc., Westbury, NY (US)

( * ) Notice: Subject to any disclaimer, the term of this patent is extended or adjusted under 35 U.S.C. 154(b) by 98 days.

(21) Appl. No.: 10/386,870

(22) Filed: Mar. 12, 2003

(65) Prior Publication Data

US 2003/0144690 A1 Jul. 31, 2003

Related U.S. Application Data

(63) Continuation of application No. 09/435,583, filed on Nov. 8, 1999, now Pat. No. 6,572,621, which is a continuation of application No. 08/955,421, filed on Oct. 22, 1997, now Pat. No. 5,997,540, which is a continuation of application No. 08/711,129, filed on Sep. 9, 1996, now abandoned, which is a continuation of application No. 08/396,261, filed on Feb. 27, 1995, now Pat. No. 5,554,103, which is a continuation of application No. 08/058,394, filed on May 6, 1993, now abandoned.

(51) Int. Cl.$^7$ ................................................ A61B 5/00
(52) U.S. Cl. ............................................ 606/64; 601/152

(58) Field of Search ............ 606/64, 201; 601/148–152; 600/311

(56) References Cited

U.S. PATENT DOCUMENTS

| 5,095,912 A | * | 3/1992 | Tomita ...................... 600/485 |
| 5,554,103 A | * | 9/1996 | Zheng et al. ................ 601/152 |

* cited by examiner

*Primary Examiner*—Kevin T. Truong
(74) *Attorney, Agent, or Firm*—Harness, Dickey & Pierce, P.L.C.

(57) ABSTRACT

The present invention provides a method for applying external counterpulsation to a patient, including detecting a blood-flow impedance signal, self-adaptive filter processing the detected blood-flow impedance signal, and adjusting inflation of an inflatable member based on the self-adaptive filter processing in order to optimize counterpulsation timing. The present invention further includes an external counterpulsation apparatus providing a high-frequency current source applied to the patient to produce an electrocardiographic signal and a blood flow impedance signal, as well as an amplifier-filter circuit to operably condition the electrocardiographic signal and a heart impedance signal amplifier receiving the blood flow impedance signal. A computer processes the signals and controls a fluid distribution device to distribute compressed fluid to a plurality of inflatable members based on said processed signals.

12 Claims, 9 Drawing Sheets

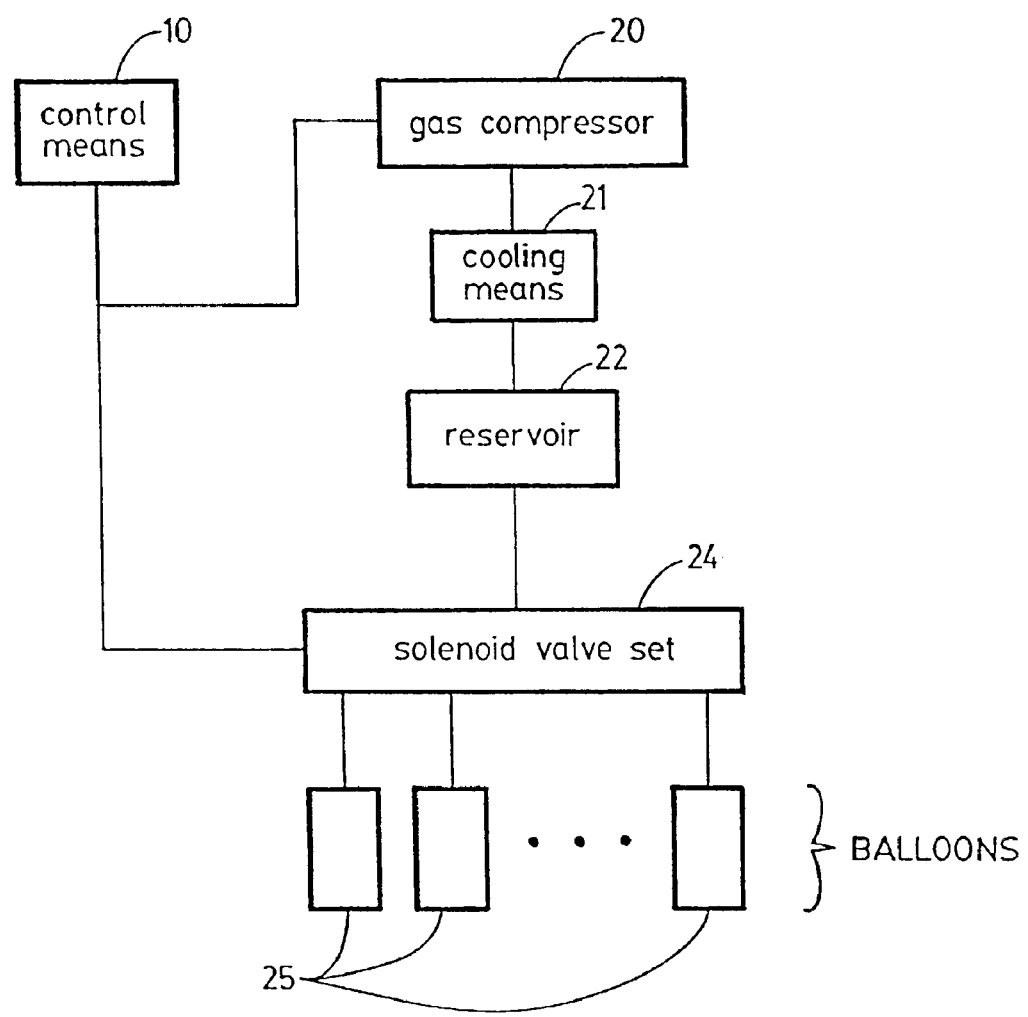
FIG._1.

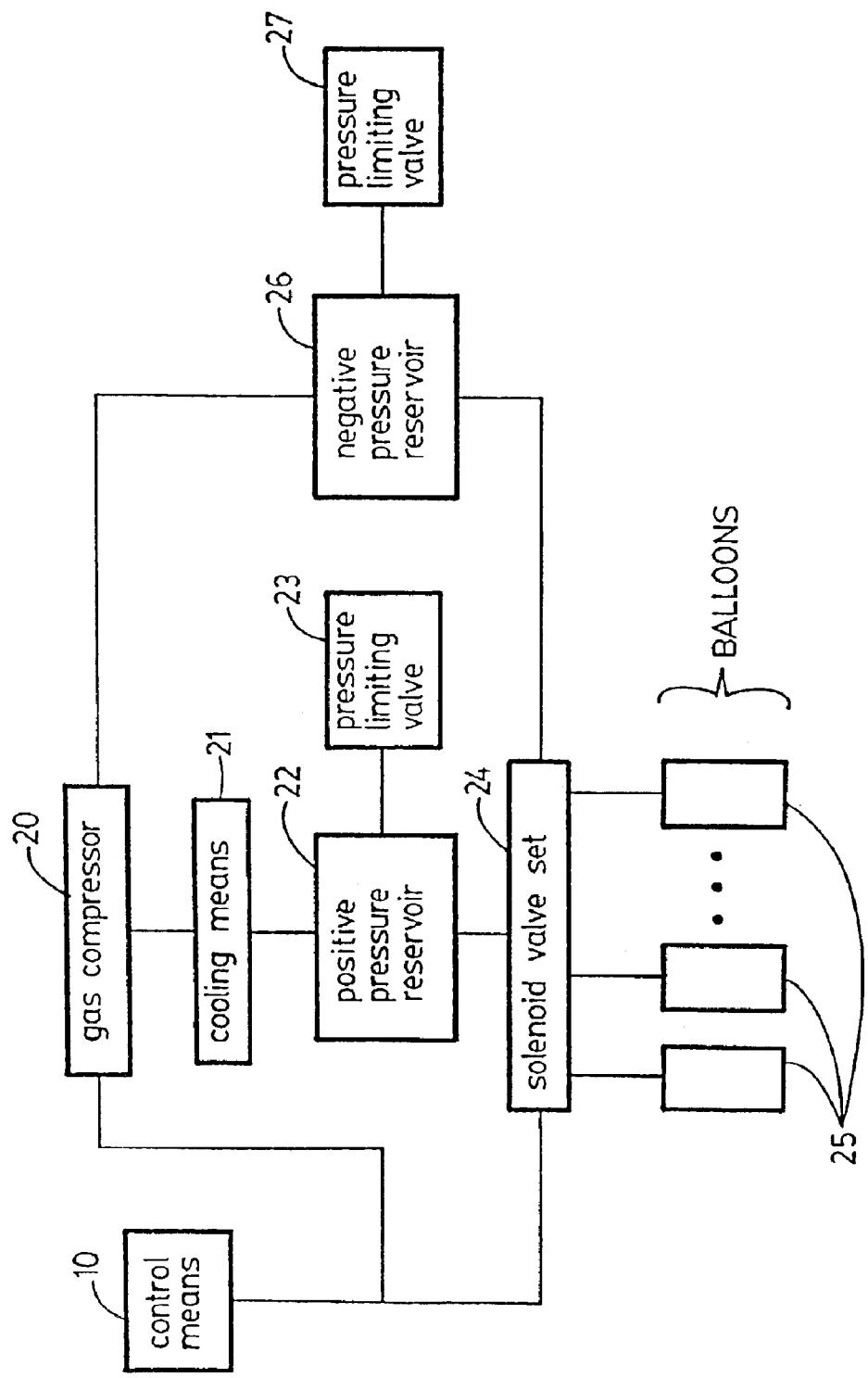
FIG._2.

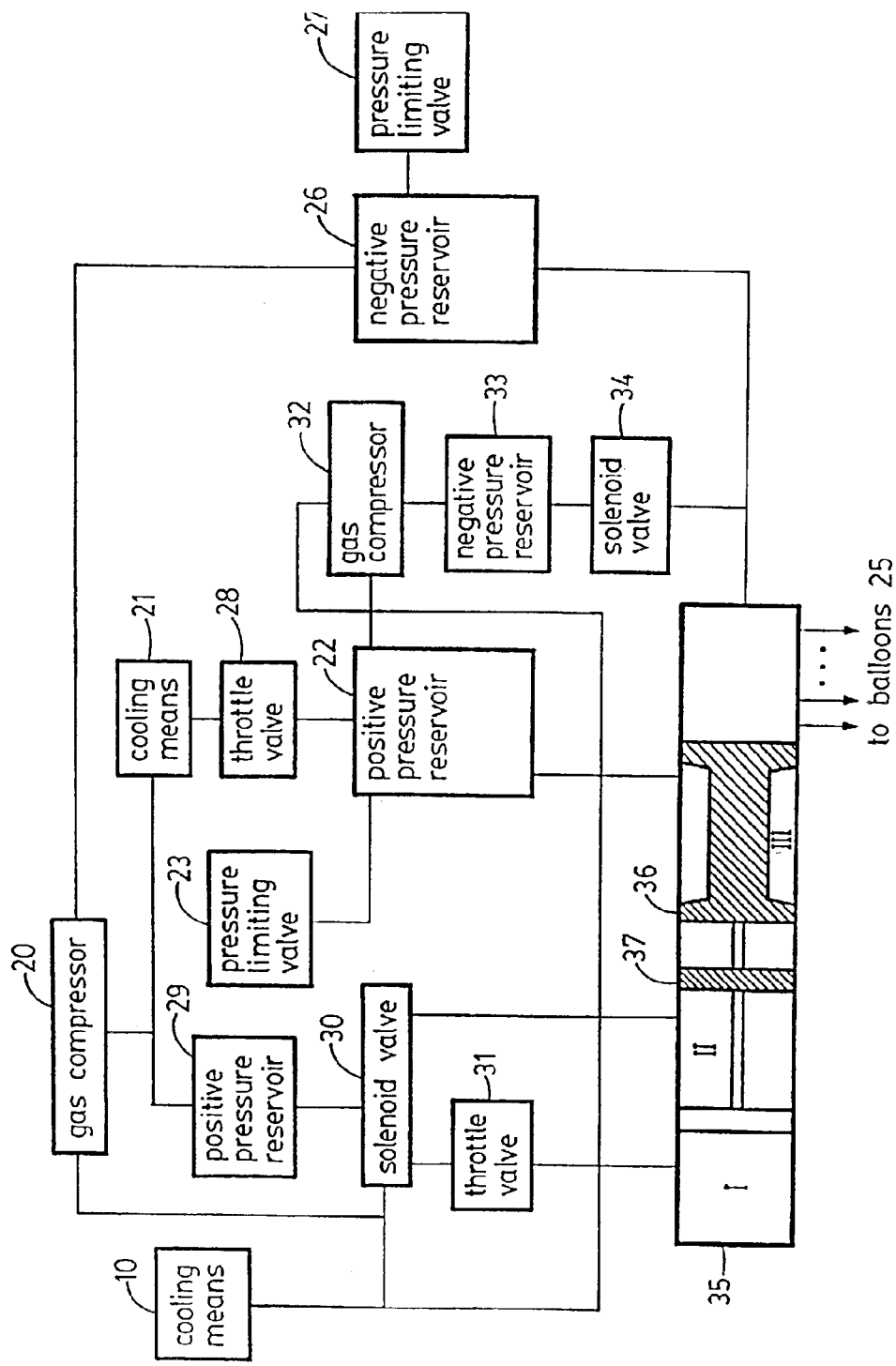
FIG._3.

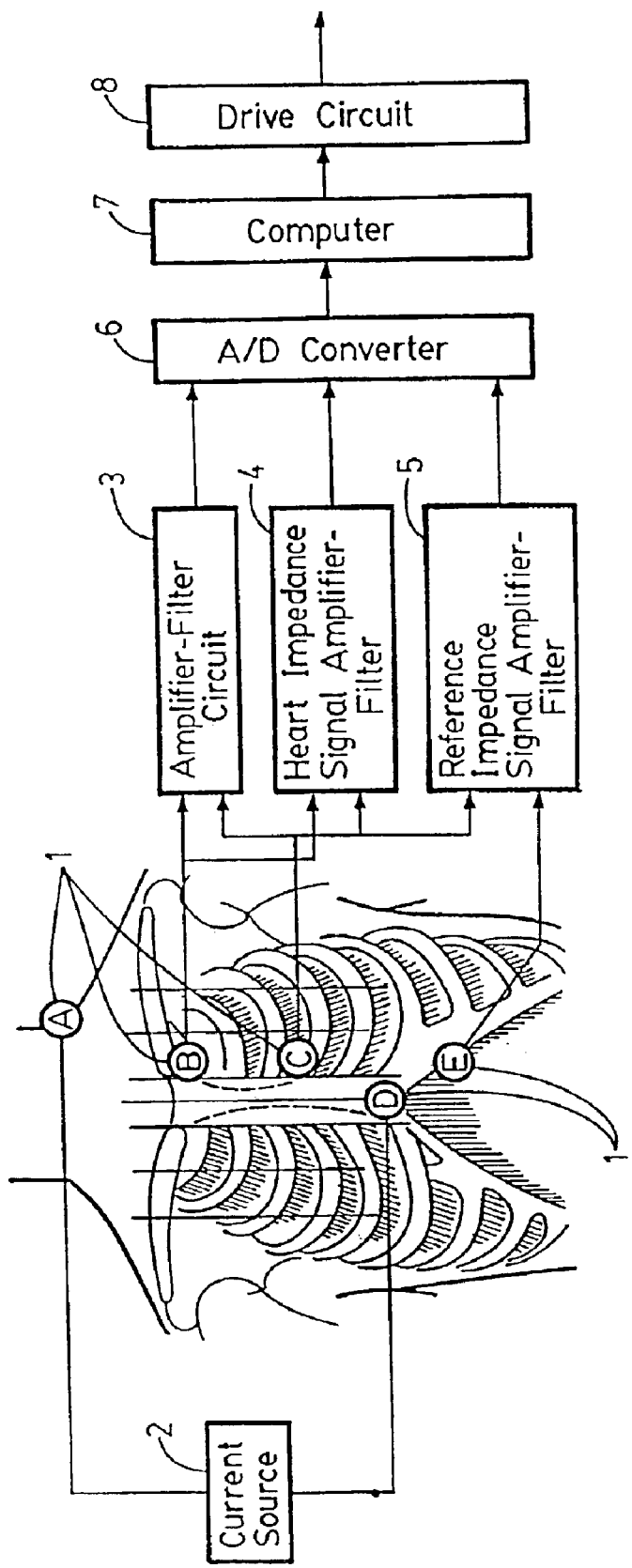
FIG._4A.

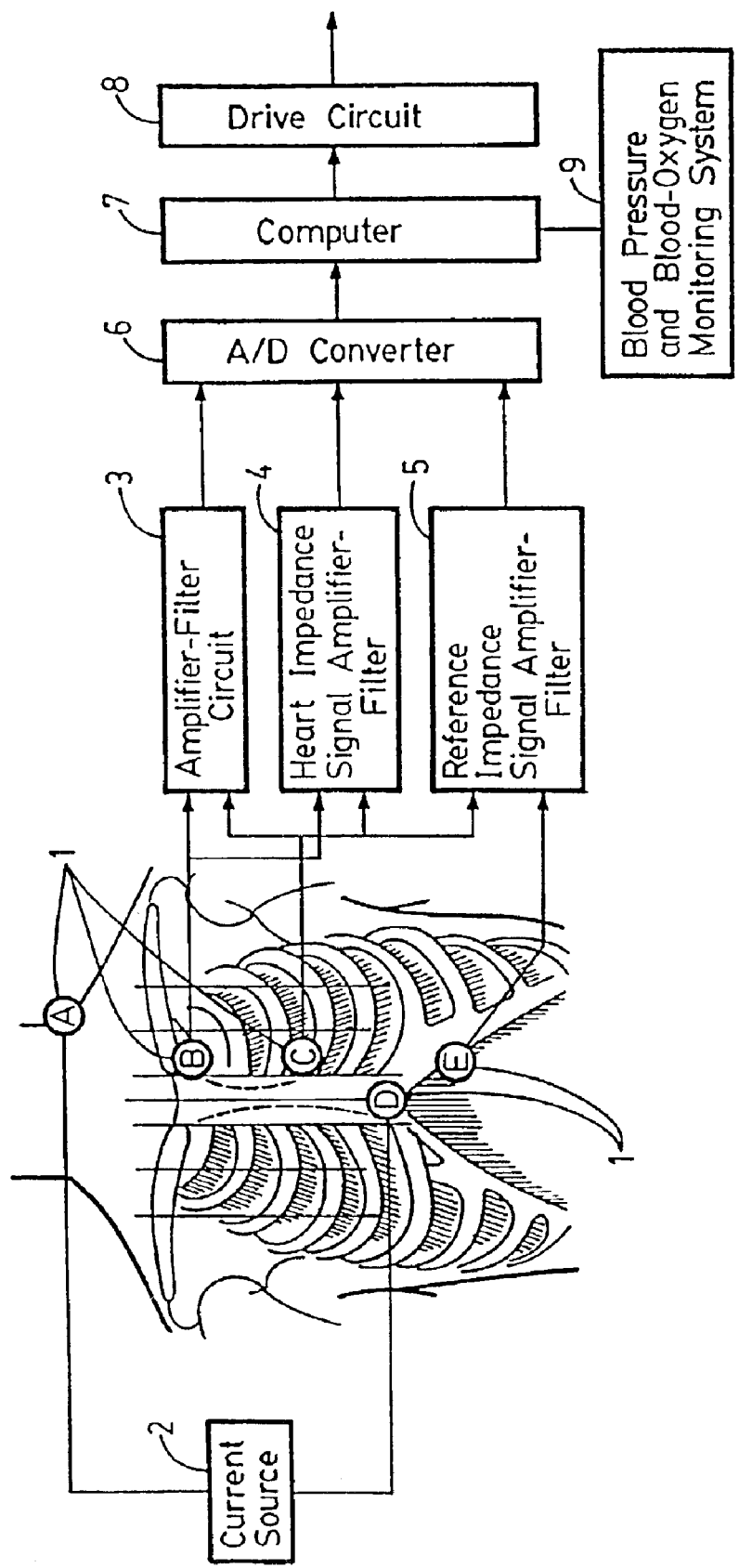
FIG._4B.

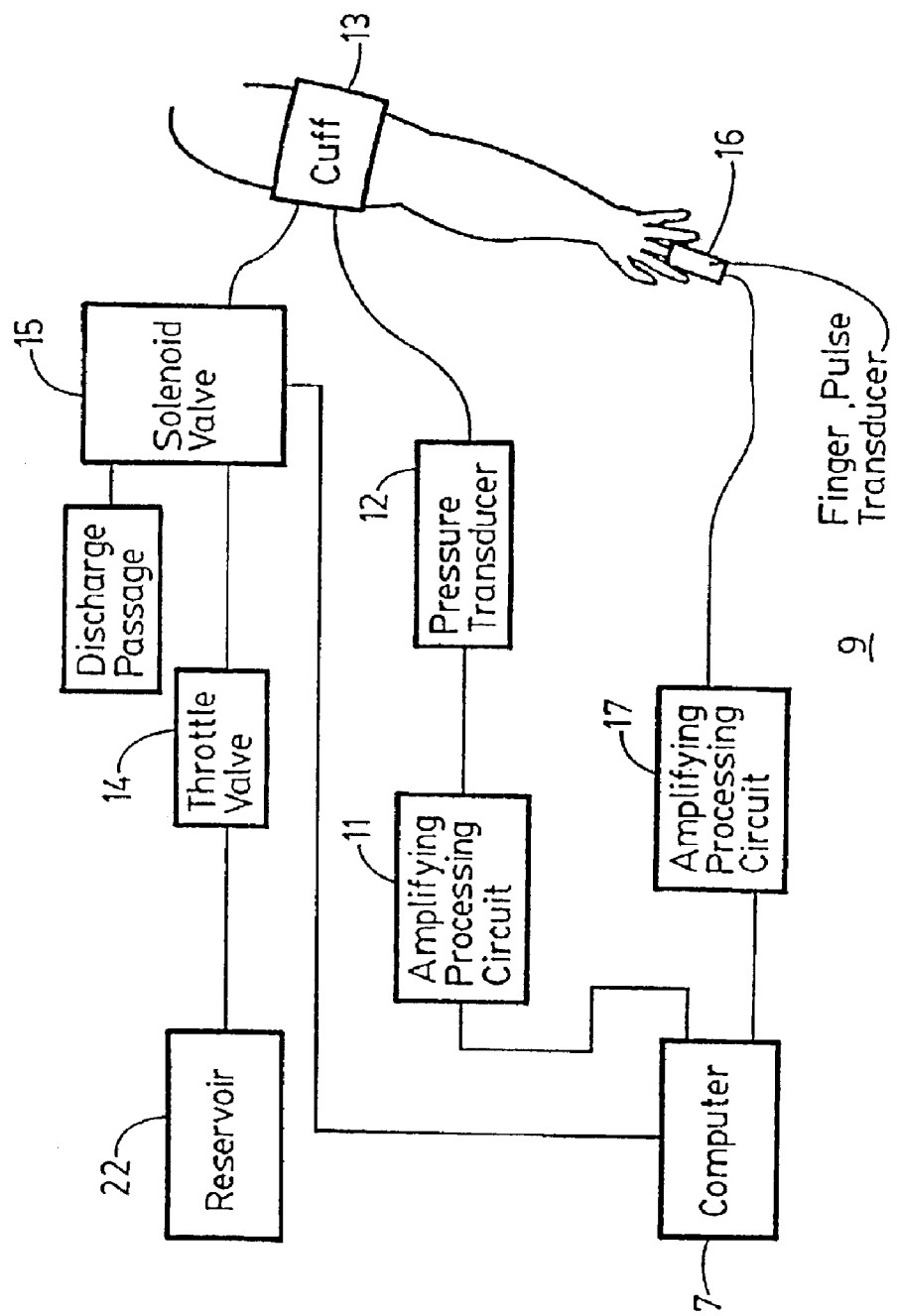
FIG._4C.

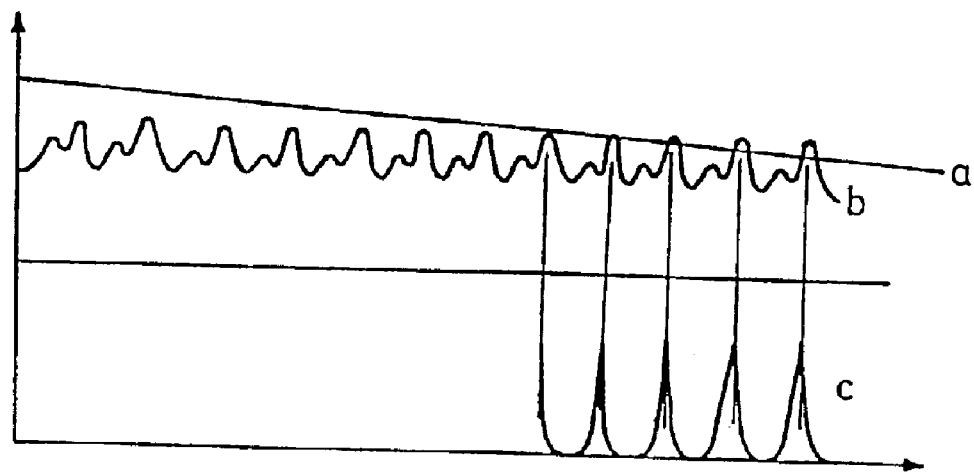
FIG._4D.
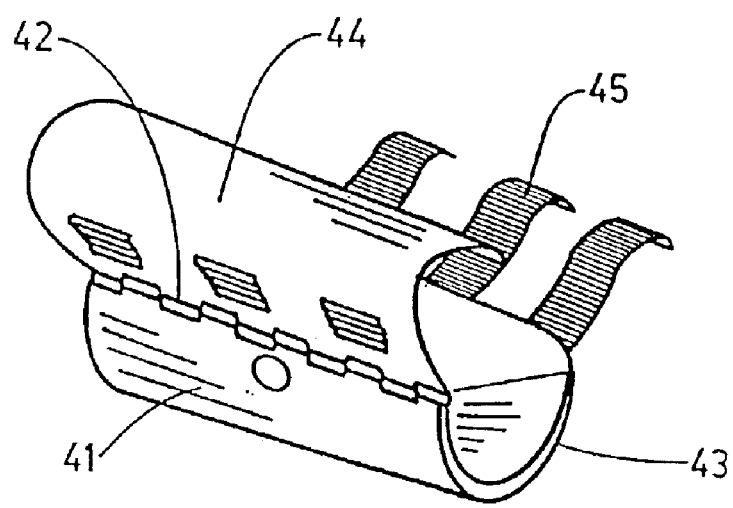
FIG._6.

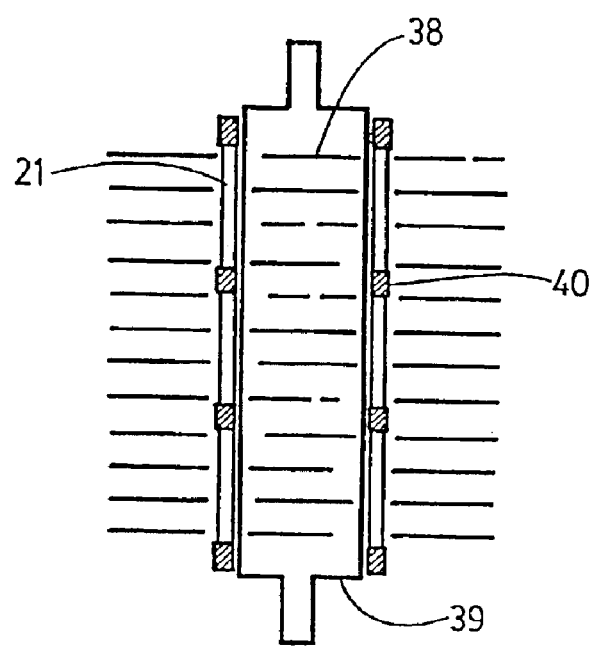
FIG._5A.
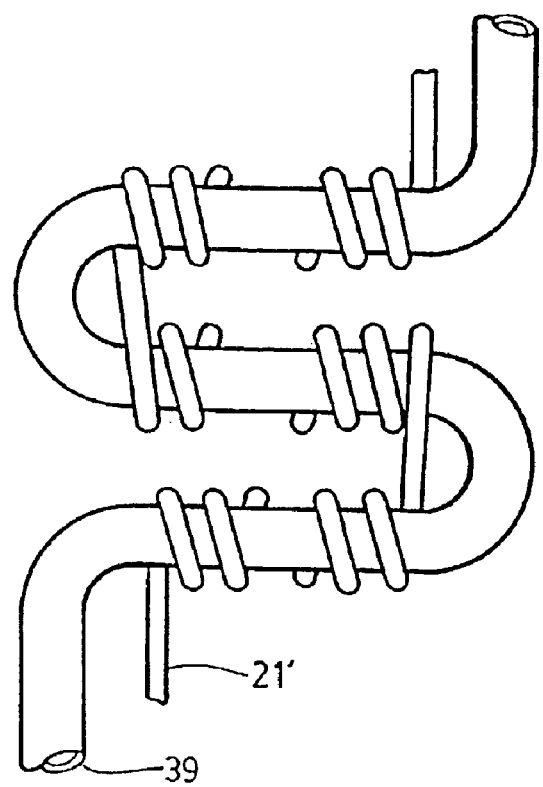
FIG._5B.

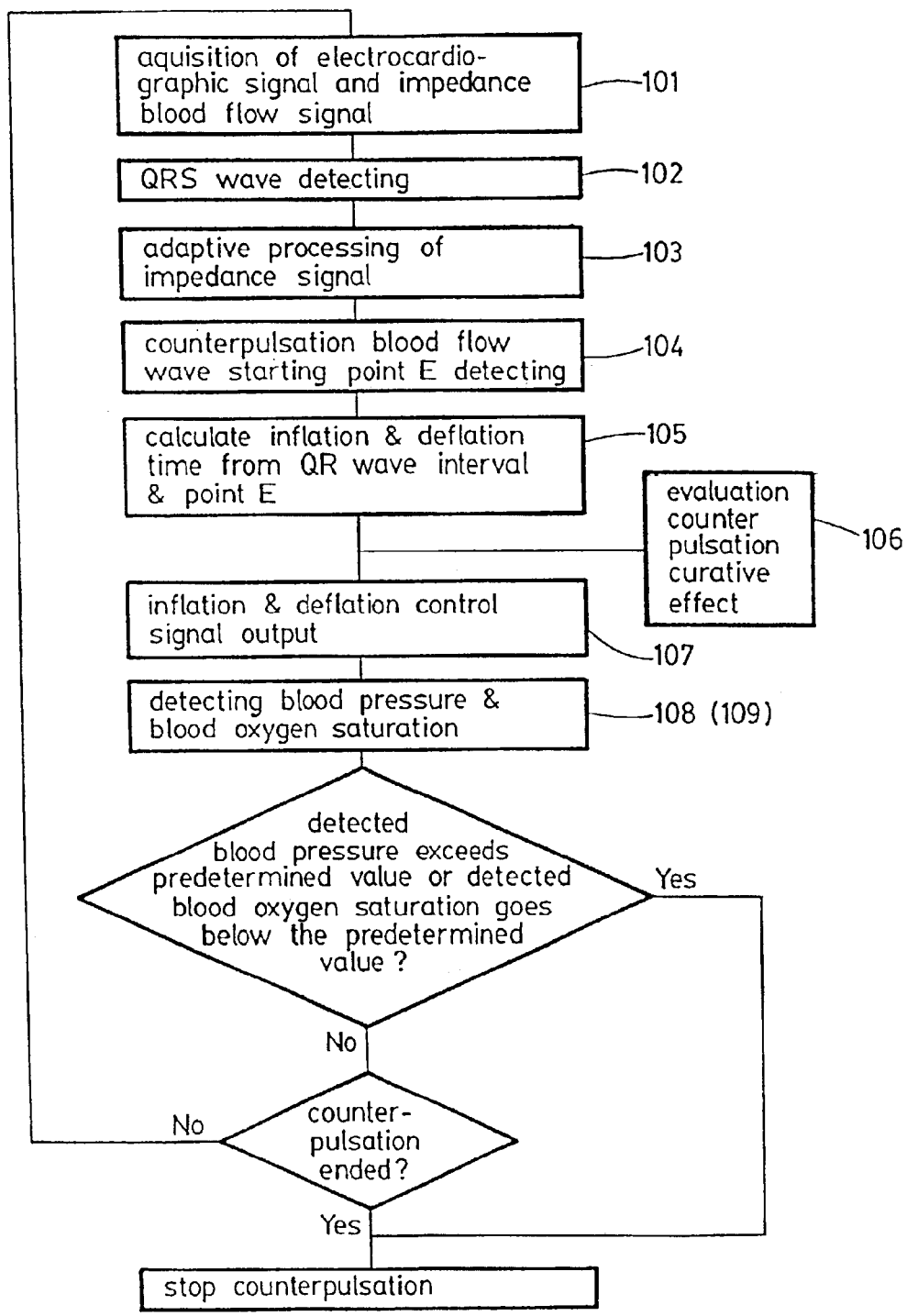
FIG._7.

HIGH EFFICIENCY EXTERNAL COUNTERPULSATION APPARATUS AND METHOD FOR CONTROLLING SAME

CROSS-REFERENCE TO RELATED APPLICATIONS

This application is a continuation of U.S. patent application Ser. No. 09/435,583 filed on Nov. 8, 1999, now U.S. Pat. No. 6,572,621, which is a continuation of U.S. patent application Ser. No. 08/955,421 filed on Oct. 22, 1997, now U.S. Pat. No. 5,997,540, which is a continuation of U.S. patent application Ser. No. 08/711,129 filed on Sep. 9, 1996, now abandoned, which is a continuation of U.S. patent application Ser. No. 08/396,261 filed on Feb. 27, 1995, now U.S. Pat. No. 5,554,103, which is a continuation of U.S. patent application Ser. No. 08/058,394 filed on May 6, 1993, now abandoned. The disclosures of the above applications are incorporated herein by reference.

FIELD OF THE INVENTION

The present invention relates to an external counterpulsation apparatus and method for controlling the same, more particularly, to an improved efficiency external counterpulsation apparatus and method for controlling the same.

BACKGROUND OF THE INVENTION

External counterpulsation provides tangible curative effect in the treatment of cardiovascular diseases, which have become more and more prevalent in recent years. In American Cardiovascular Journal (30(10)656–661, 1973) Dr. Cohen reported a device for external counterpulsation, being a four-limb sequential counterpulsation device. It consists of multiple balloons wrapped around the four limbs of the patient. Pressure is applied sequentially from the distal to the proximal portion of each limb. Using high pressure gas from a large compressor as its energy source (1000 to 1750 mm Hg) to control the opening time of a solenoid valve, the balloons receive pressurized air during inflation. The balloons are deflated by use of a vacuum pump. The device requires the use of a large air compressor, a large vacuum pump and the use of numerous pressure transducers to monitor the input pressure to insure that no excessive pressure is exerted in the balloons. However, this device is not only bulky and expensive, but it is also extremely noisy and complicated to operate. It is, therefore, unsuitable for everyday clinical use.

External cardiac assistance has been described in U.S. Pat. No. 3,866,604, which is an improvement on the above original external counterpulsation device. However, this device is extremely bulky, noisy, and complicated to operate.

An external counterpulsation apparatus has also been described in Chinese Patent CN85200905, which has been granted as U.S. Pat. No. 4,753,226. This external counterpulsation apparatus is regarded as another improvement over previous art. In addition to balloons for the four limbs, it also comprises a pair of buttock balloons. The balloons are sequentially inflated with positive pressure and then, with appropriate delay, simultaneously deflated using a microcomputer to control the opening and closing of solenoid valves. The high pressure gas source and vacuum pump have been eliminated so as to reduce the volume of the apparatus and make it more practical. However, the deflation of the balloons of this apparatus lacks the suction of negative pressure and depends on natural exhaustion into the atmosphere. Therefore, the exhaustion of the balloons is incomplete and slow, and leaves behind residual gas in the balloon which hinders the ability of this device to reduce afterload (workload) of the heart.

A positive and negative enhanced type external counterpulsation apparatus has been described in Chinese Patent CN88203328, wherein a negative pressure suction means for exhaustion of the balloons has been added. However, this apparatus is still ineffective in the exhaustion of all the pressurized gas in the balloons and in addition, it is still too large, noisy and heavy for transport to be of practical application in the clinical setting.

A miniaturized external counterpulsation apparatus has been described in Chinese Patent CN1057189A, wherein the air compressor can be placed inside the main body of the device and does not require a separate embodiment. The box containing the solenoid valves and the balloon cuffs are suspended in a tube like apparatus and directly attached to the main body of the device. This device is practical for clinical use in that its size is very much reduced. However, this device does not have negative suction to increase the rate of deflation of the balloons, and it is still extremely noisy and not very efficient in producing desirable counterpulsation hemodynamic effects, namely a high rate of inflation and effective deflation.

The foregoing external counterpulsation apparatuses have many advantages over the original one, but there are still many problems. For example, the high pressure air produced by the air compressor has a high temperature when it arrives at the balloons, which may cause a feeling of discomfort or even pain for the patient; the balloon cuff used by the prior art external counterpulsation apparatus is made of soft materials such as leatherette, canvas and the like, which may have a high elasticity and extensibility, requiring the use of a large volume of gas to achieve the required pressure and resulting in the inability to quickly inflate the balloons for optimal rate of inflation. Furthermore, dead space may be formed due to the misfit between the balloon cuff and the surrounded limb; the balloon cuff could slip downward during counterpulsing, thereby being incapable of efficiently driving blood from peripheral regions to the root of the aorta, which directly affects the effectiveness of the counterpulsation treatment. All these factors reduce the efficiency of counterpulsation and require more pressurized gas to fill up dead space and more power from the compressor. At the same time a reduction in the rate of inflation of the balloon results in hindering the effective compression of the body mass as well as vasculature.

Historically, the earlobe pulse wave, finger pulse or temporal pulse wave are used in a timing signal to give the appropriate time for application of the external pressure so that the resulting pulse produced by external pressure in the artery would arrive at the root of the aorta just at the closure of the aortic valve, which divides the arterial pulse wave into a systolic period and a diastolic period. However, earlobe pulse wave, finger pulse wave or temporal pulse wave are signals derived from microcirculation and may not reflect the true pulse wave from the great arteries such as the aorta. Using the dicrotic notch as the true aortic valve closure is incorrect because the dicrotic notch is affected by many other factors such as the dampening effect of the vascular elasticity, reflective wave from tapering of the arteries and interference from previous pulse waves. Therefore, it is most important in the art of external counterpulsation to find the true aortic valve closure time so the appropriate inflation time can be found for the externally applied pressure.

Theoretically, there are two factors that should be taken into account to determine the appropriate deflation time of all the balloons simultaneously: (1) release of all external pressure before the next systole to produce maximal systolic unloading, that is the maximum reduction of systolic pressure; and (2) maintenance of the inflation as long as possible to fully utilize the whole period of diastole so as to produce the longest possible diastolic augmentation, that is the increase of diastolic pressure due to externally applied pressure. Therefore, one measurement of effective counterpulsation is the ability to minimize systolic pressure, and at the same time maximize the ratio of the area under the diastolic wave form to that of the area under the systolic wave form. This consideration can be used to provide a guiding rule for determination of optimal deflation time.

Furthermore, the various existing external counterpulsation apparatuses only measure the electrocardiograph signals of the patient to guard against arrhythmia. Since counterpulsation applies pressure on the limbs during diastole, which increases the arterial pressure in diastole and makes it higher than the systolic pressure, the blood flow dynamics and physiological parameters of the human body may vary significantly. Some of these variations may be advantageous, while some of them are potentially unsafe. For patients with arteriosclerosis and phelbosclerosis, there is the danger of blood vessels breaking due to the increase in their internal pressure. Furthermore, applying pressure to the limbs presses not only on the arteries but also the veins, and this may result in an increase in the amount of blood returning to the heart. This may cause cardiac, lung or pulmonary edema because of the degration of the decrease in pumping capacity of the heart and incapability of the heart to pump out the increased amount of blood returning to the heart. This may, in turn, affect the oxygen saturation in the arteries of the body and cause an oxygen debt. It is, therefore, necessary to monitor the maximum value of the arterial pressure and oxygen saturation in the blood of a patient in addition to monitoring the electrocardiogram to ensure safety of the patient during the counterpulsation treatment.

Furthermore, the gas distribution device in the existing external counterpulsation apparatuses operate by controlling the opening and closing of the solenoid valves, which has the disadvantage of having voluminous and complex pipe connections. This is disadvantageous to miniaturizing the whole apparatus and improving its portability.

SUMMARY OF THE INVENTION

The method for applying external counterpulsation according to the invention includes detecting a blood flow impedance signal, which is self-adaptive filter processed, then adjusting inflation of an inflatable member based on the self-adaptive filter processed blood flow impedance signal to optimize counterpulsation timing. The self-adaptive filter processing includes comparing a reference impedance signal to a detected impedance signal. Adjusting inflation of the inflatable member includes adjusting inflation to coincide retrograde blood flow signals with aortic valve closure.

The external counterpulsation apparatus according to the invention includes a plurality of inflatable members adapted to be received about a limb of the patient, a source of compressed fluid in fluid communication with a plurality of inflatable members, and a fluid distribution device connected to the inflatable members and operable to distribute compressed fluid from the source of compressed fluid to the inflatable members. A high-frequency current source is applied to the patient to produce electrocardiographic signals and blood flow impedance signals. An amplifier-filter circuit conditions the electrocardiographic signals received from the patient. The heart impedance signal amplifier receives blood flow impedance signals from the patient. The computer processes the electrocardiographic signals and the blood flow impedance signals in order to control the fluid distribution device based on the processed electrocardiographic signals and blood flow impedance signals. The amplifier filter circuit includes a low-pass differential amplifier and a band-pass filter for amplifying and filtering the electrocardiographic signals received from the patient. The computer detects a QRS wave from the electrocardiographic signals and performs adaptive processing of the impeded blood flow signal. To do so, the computer uses an impedance reference signal to adaptively process the impedance blood flow signal. The computer also determines electrocardiographic characteristic points, including aortic valve closure, diastolic amplitude, and systolic amplitude. The external counterpulsation apparatus also includes a drive circuit electrically controlled by the computer to inflate and deflate the plurality of inflatable members. A pulse transducer is electrically connected to the computer for detecting a pulse wave, and a pressure transducer is electrically connected to the computer for detecting a maximum arterial pressure. The computer processes the pressure and pulse signals and controls counterpulsation based on the process signals. The computer also calculates oxygen saturation based on the processed pressure and pulse signals.

A counterpulsation control method according to the invention includes obtaining an impedance blood flow signal, obtaining an electrocardiographic signal, detecting a QRS wave of said electrocardiographic signal, determining a counterpulsation blood flow wave initiation from said impedance blood flow signal, and controlling at least one of inflation time and deflation time of an inflatable member from said electrocardiographic signal and said counterpulsation blood flow wave initiation. The method may further include determining an objective index reflecting a curative effect of counterpulsation. The objective index includes determining a peak amplitude and duration of a systolic wave form and an impedance cardiograph counterpulsation wave. The method further includes applying a high frequency constant current source to a patient body to generate the impedance blood flow signal and the electrocardiographic signal. The impedance blood flow signal and electrocardiographic signal may be displayed. The method may further include adaptive processing of the impedance blood flow signal, as well as determining a counterpulsation blood flow wave initiation by processing the impedance blood flow signal after self-adaptive filter processing. The method may also include detecting blood pressure, as well as comparing detected blood pressure to a predetermined value. The method may include stopping counterpulsation if the detected blood pressure exceeds the predetermined value. The method optionally includes detecting blood oxygen saturation.

BRIEF DESCRIPTION OF THE DRAWINGS

The present invention will become more fully understood from the detailed description and the accompanying drawings, wherein:

FIG. 1 is a block diagram of a first embodiment of the external counterpulsation apparatus according to the present invention;

FIG. 2 is a block diagram of a second embodiment of the external counterpulsation apparatus according to the present invention;

FIG. 3 is a block diagram of a third embodiment of the external counterpulsation apparatus according to the present invention;

FIGS. 4A and 4B are detailed block diagrams of the control means in the external counterpulsation apparatus according to the present invention;

FIG. 4C is a detailed block diagram of the blood pressure and blood oxygen monitoring means illustrated in FIG. 4B;

FIG. 4D is a schematic diagram showing the relationships between the variation of cuff pressure, finger pulse wave, and opening and closing of the aortic valve;

FIGS. 5A and 5B are partial schematic diagrams of the gas source portion in the external counterpulsation apparatus according to the present invention, illustrating gas pipes connected to a semiconductor cooling device and air-conditioner cooling evaporator, respectively;

FIG. 6 is a schematic diagram of the balloon device used in the external counterpulsation apparatus according to the present invention, illustrating an improved structure of the balloon cuff body; and FIG. 7 is a flow chart of the method for controlling the external counterpulsation apparatus according to the present invention.

DETAILED DESCRIPTION OF THE PREFERRED EMBODIMENTS

The following description of the preferred embodiment(s) is merely exemplary in nature and is in no way intended to limit the invention, its application, or uses.

A detailed description of the present invention follows with reference to the accompanying drawings in which like elements are indicated by like reference numerals.

FIG. 1 is the block diagram of a first embodiment of the external counterpulsation apparatus according to the present invention, wherein a control means 10 controls the gas compressor 20 and set of solenoid valves 24. The compressor can be of rotary vane type, piston type, diaphragm or blower type. However, the preferred embodiment would be a scroll type compressor as described in the Chinese Patent CN1030814A, which essentially consists of two scroll basins with very narrow gaps between them; with one scroll basin adapted to rotate at a very high speed (3,000 rpm) while the other scroll basin remains stationary. The clenching of the scroll basins compresses the air radially inwardly toward the center and the compressed air comes out of the center shaft. The scroll type of compressor is more efficient in operation, more quiet and smaller in size than other types of compressors and, therefore, is suitable for the external counterpulsation apparatus described hereof. During operation, the compressor 20 operates to produce pressurized gas which is sent into the positive pressure reservoir 22 via the cooling means 21. A pressure limiting valve 23 is provided on the reservoir 22, which keeps the internal pressure of the reservoir 22 constant. The opening and closing of the set of solenoid valves 24 is controlled by the inflation and deflation driving signals generated by the control means in accordance with the heart impedance blood flow graph of the human body. The set of solenoid valves 24 includes a number of two-position, three-way solenoid valves corresponding to the number of balloons 25. When a valve is in the first of the two positions, it inflates its balloon. When it is in the second of the two positions, it deflates its balloon, under control of the control means.

FIG. 2 illustrates a second embodiment of the external counterpulsation apparatus according to the present invention. In this embodiment, a control signal is first generated by the control means 10, then the compressor 20 operates to compress gas into the positive pressure reservoir 22 after being cooled by the cooling means 21. A pressure limiting valve 23 is provided on the positive pressure reservoir to keep its internal pressure constant. A negative pressure reservoir 26 connected to the inlet of the compressor 20 produces negative pressure. The control means 10 controls the opening and closing of the set of solenoid valves 24 by issuing inflating and deflating driving signals in accordance with the results of detection. Again, when the set of solenoid valves 24 are in the first position, they inflate the balloons 25. When they are in the second position, they deflate the balloons 25. The gas discharged from the balloons is discharged into the negative pressure reservoir 26 via the set of solenoid valves 24, and then returns to the compressor 20. As there may be leakage during the circulation of gas, which may affect the amount of gas output from the compressor, a pressure limiting valve 27 is provided to adjust the negative pressure in the negative pressure reservoir. When the negative pressure exceeds a certain value, the pressure limiting valve 27 is opened to inject a certain amount of gas into the reservoir 26.

FIG. 3 illustrates a third embodiment of the external counterpulsation apparatus according to the present invention; wherein the control means 10 generates control signals and the compressor 20 operates to produce two portions of pressurized gas, one portion of pressurized gas is sent to the positive pressure reservoir 29, while another is sent into the positive pressure reservoir 22 via the cooling means 21 and the throttle valve 28. The pressure limiting valve 23 is operative to adjust the pressure inside the reservoir 22. The reference numeral 30 indicates a two-position, five-way solenoid valve or two two-position, three-way solenoid valves, 31 indicates a mono-directional throttle valve, 35 indicates a cylindrical gas distribution means or cylinder, 37 is a partition and 36 indicates a piston. When an inflation driving signal is issued by the control means, the solenoid valve 30 opens to the first of the two positions, and the gas flow is introduced into the portion I of the cylinder from the reservoir 29 via the solenoid valve 30 and the throttle governor 31 to push the piston from a first end towards a second end of the cylinder. A space portion III is formed by the piston and the cylinder and is always in communication with the reservoir 22, and vents for the balloons 25 are situated in sequence in the cylinder, the balloons being sequentially inflated as the piston moves towards the second end of the cylinder. When a deflation signal is issued by the control means, the solenoid valve 30 is moved to its second position, and the gas in the reservoir 29 enters the portion II of the cylinder via the solenoid valve 30 to push the piston back to the first end of the cylinder. At that time, the gas in portion I is discharged via the solenoid valve 30, and the gas in the balloons is discharged to the negative pressure reservoir 26. In order to speed deflation, a solenoid valve 34 is also opened at the same time and the gas discharged from the balloons is discharged to both negative pressure reservoirs 26 and 33. Negative pressure reservoir 33 is kept at a negative pressure by the input portion of compressor 32. Discharged gas is also sent to the reservoir 22 by the output portion of compressor 32.

During the deflation phase, if the pressurized balloon is simply exhausted into the atmosphere, exhaustion of the balloon may not be completed, with the residual gas pressing on the tissue mass surrounded by the balloon cuffs, reducing the much needed vascular space in the body to receive the volume of blood ejected by the heart. This reduces the ability of counterpulsation to unload systolic blood pressure and reduces cardiac workload. The addition of negative pressure reservoirs 26, 33 serves to effectively and rapidly evacuate the pressurized gas in the balloons at the onset of systole, thereby ensuring complete absence of pressure on the lower extremities, enabling the vasculature which has been previously compressed and emptied during the diastolic period to act as suction to help the heart to eject blood out and unload the systolic blood pressure. In addition, and equally important, the addition of the negative pressure reservoirs 26, 33 ensures the smooth operation of the solenoid valves and prevents the leakage of large volumes of pressurized gas exhausting into the atmosphere. This closed gas system reduces the escape of noises generated by the opening and closing of solenoid valves and movement of air.

Furthermore, during normal operation of external counterpulsation, there is always some leakage of compressed air from the balloon during the inflation period. In order to compensate for the leakage of air to ensure there is adequate air for the intake of the compressor 20 to produce air pressure in the range of 5 to 15 psi, a leakage compensation means such as the use of a vacuum limiting valve, a vacuum pump or compressor or some combination thereof is provided. An example of the compensation means is a vacuum limiting valve 27 connected to the negative pressure reservoir 26, set at approximately negative 100 mm Hg. When the negative pressure reservoir is less that 100 mm Hg, the vacuum limiting valve is open and air is sucked into the reservoir to provide more air for the intake of the compressor 20.

Prior art in external counterpulsation make use of bulky, noisy and power consuming solenoid valves are normally closed to reduce the generation of heat in keeping them open. However, this situation would induce danger to the patient in case of power failure if compressed gas is trapped in the balloons.

This invention provides a gas cylindrical distribution system 35 as shown in FIG. 3, using a syringe system in pushing a piston in one direction to provide sequential inflation of the balloons, with the balloons 25 (not shown) furthest from the heart being inflated first. The balloon openings are placed on both sides of the cylinder, connecting to the left and right limbs as well as buttock. The number of balloons can be 2 to 8 or more on each side. This is achieved by connecting the balloons furthest from the heart to the portion of the cylinder closest to the piston, as the piston 36 moves from left to right as shown in FIG. 3. This gas distribution system uses compressed air to move a piston back and forth along a cylindrical means, producing a quiet operation without the need of too much power as compared to the use of bulky, noisy and power consuming solenoid inflation and deflation valves, thereby eliminating one of the most noisy parts of the prior art external counterpulsation apparatus, and reducing substantially the consumption of electric power. More importantly, the solenoid valve 30 is a normally open valve of portion 11 of the cylinder 35, thereby connecting portion II to the positive pressure reservoir 29 in case of power failure, moving the piston to the left of FIG. 3, exposing all the balloons to the negative pressure reservoir, thereby deflating all balloons and reducing the possibility of inducing trauma to the patient.

FIGS. 4A and 4B are detailed block diagrams of the control means in the external counterpulsation apparatus according to the present invention. Using impedance cardiography as the control means in detecting blood flow in the great arteries, the precise closure of the aortic valves is coordinated with the pulse wave generated by external counterpulsation pressure in the external counterpulsation apparatus according to the present invention, wherein reference numeral 1 indicates electrodes. The locations and types of electrodes used are for illustrative purpose and should not be considered as constraint to such design and configuration.

The detecting electrode 1 consists of five point electrodes placed in the positions shown in FIG. 4A, that is, electrode A positioned at the root of the left ear or mastoid, electrode D positioned at the xiphoid process, electrode B positioned at the lift edge of the left sternum below the clavicle and electrode C positioned at the lift edge of the left sternum between the fourth and fifth ribs. Electrodes A and D are both impedance current electrodes, high frequency constant current being applied to the body from these two electrodes. Electrodes B and C are both detector electrodes for measurement of the blood flow impedance signals which may be derived from blood flow in the great arteries in the thoracic space. A reference electrode E is positioned in the left anterior of the 10th rib. The signal obtained between electrodes C and E will be used as the reference signal for measuring movement of the body, especially motion artifact produced during the application of external counterpulsation pressure. The location of the reference electrode E is not important but should be further away from the thoracic space.

Before the start of external counterpulsation treatment, high frequency constant current is applied to electrodes A and D, and blood flow impedance signals related to the blood flow in the great arteries in the thoracic space will be picked up by detector electrodes B and C; these blood flow impedance signals also contain a dip in the wave form indicating the closure of the aortic valves.

Because of the location of the reference electrodes pair C and E, the blood flow impedance signals detected between these electrodes will be much weaker than the signals detected by electrodes B and C. Upon initiation of external counterpulsation, there will be two additional signals detected by both pairs of detected electrodes B, C and reference electrodes C and E. They are the retrograde blood flow impedance signals produced by the counterpulsation pressure, and the motion artifact produced by the same. The signals from motion artifact will present themselves to both pairs of electrodes in approximately equal amplitudes, while the signals from counterpulsation will be larger in the reference electrodes than in the detector electrodes because of the location of the reference electrodes in closer proximity to the counterpulsation hemodynamic effects. Consequently, subtraction of reference impedance signals from the detector impedance signals will provide a fairly clean blood flow impedance signal containing the time of aortic valves closure as well as the retrograde flow from counterpulsation. This kind of signal processing is known as self-adaptive filtering processing. By adjusting the onset of the inflation of the balloons, the retrograde blood flow signals can be advanced or retreated to coincide with the aortic valves closure, thereby providing optimal counterpulsation timing. In addition, the adjustment of the optimal timing can also be performed by computer.

A high frequency constant current source 2 consists of: a transistor oscillator, amplitude limiting amplifier, band-pass filter and voltage-current converter to obtain a stable high frequency and stable amplitude current which is applied to the body by electrode A to measure the impedance.

An amplifier-filter circuit 3 for the electro-cardiographic signal consists of: a low-pass differential amplifier and band-pass filter-amplifier, which amplifies and filters the electrocardiographic signals of the body obtained from electrodes B and C.

A heart impedance signal amplifier-filter circuit 4 and a reference impedance signal amplifier-filter circuit 5 for adaptive processing consist of a band-pass filter-amplifier, a detector, a low-pass filter, and a differential circuit. The signal amplifier-filter circuits amplify and filter the heart impedance blood flow signals obtained from the electrodes B and C, and the adaptive processed impedance reference signals obtained from the electrodes C and E.

A computer system consists of a personal micro-computer 7 and an A/D converter 6. The A/D converter converts the electrocardiographic signals, heart impedance blood flow signals, and impedance reference signals into digital signals and inputs them into the computer. The computer displays the waveform, detects the QRS wave of the electrocardiogram, indicates the upper and lower limits of the pulse rate, performs adaptive processing of the impedance blood flow signals and the impedance reference signals, measures the characteristic points of the waveform such as the aortic valve closure and end diastolic and systolic amplitudes, and controls the inflation and deflation time of the external counterpulsation apparatus through a drive circuit 8.

FIG. 4B is also a detailed block diagram of the control means in the external counterpulsation apparatus according to the present invention, wherein a blood-pressure and blood oxygen monitoring means 9 are further added to the basic system shown in FIG. 4A.

FIG. 4C is a schematic block diagram of the blood-pressure and blood oxygen monitoring means 9 indicated in FIG. 4B.

FIG. 4D is a schematic diagram showing the relationships between the pressure variation of the cuff, finger pulse wave, and the opening and closing of the aortic valve.

Referring to FIG. 4C, 22 indicates the reservoir of the counterpulsation apparatus, which inflates a cuff 13 via a pipe, throttle valve 14, and a passage in a solenoid valve 15. The solenoid valve is two-position, three-way valve controlled by the computer 7. The other passage of the solenoid valve is a discharging passage for the cuff, the discharge speed being controlled by the throttle valve 14. At the beginning of blood pressure measurement, the inflation passage of the solenoid valve 15 is opened, the pressurized gas in the reservoir 22 inflates the cuff 13 via the throttle valve 14 to a predetermined pressure value at which the arteries are blocked. When they are blocked, a finger pulse transducer 16 is unable to detect a pulse wave. The inflating passage of the solenoid valve 15 is closed and the deflating passage is opened, the gas in the cuff discharges slowly via the solenoid valve 15 and the throttle valve 14 and the pressure inside the cuff drops slowly as shown by curve "a" in FIG. 4D. When the pressure in the cuff is equal to or slightly lower than the maximum arterial pressure, as shown by curve "b" in FIG. 4D (systolic pressure before counterpulsation, and diastolic counterpulsation pressure during counterpulsation), the blocked blood vessels are pushed open instantaneously. At that time, the finger pulse transducer 16 will detect a rapidly varying pulse wave as shown by curve "c" in FIG. 4D. This indicates the arrival of the maximum pressure of the artery. The pressure detected by a pressure transducer 12 at that time is the maximum arterial pressure. Referring to FIG. 4C, 11 indicates an amplifying processing circuit for the pressure signal, and 17 indicates an amplifying processing circuit for the pulse signal. The amplified pressure and pulse signals are collected and processed by the computer 7 for performing corresponding counterpulsation control and calculation of oxygen saturation of blood.

It is a physical law that when air is compressed, heart will be generated. In external counterpulsation, approximately 25 cubic feet of air is compressed to 5 to 15 psi pressure, generating a gas with a temperature reaching as high as 90–100° C., depending on the environment and efficiency of the compression means. When compressed gas with such a high temperature is sent to the balloons which are in close contact with the skin of the patient, it will produce abrasion or burn to the skin, or at the least, an uncomfortable feeling to the patient. Therefore, it is essential in this invention to provide means to cool the compressed air. In general, any means of cooling can be utilized in this invention, including exposure to the atmosphere of a long piece or coil of metal pipe connecting the compression means to the positive pressure reservoir, use of a fan to force air to blow through a coil of metal pipe carrying the heated gas, water-cooling such as that used in the radiator of an automobile, running water cooling, or air conditioner.

FIGS. 5A and 5B are partial schematic diagrams of the gas source portion in the external counterpulsation apparatus according to the present invention, illustrating the gas pipes connected to a semiconductor cooling device and an air conditioner cooling evaporator, respectively. 21 and 21' indicate a semiconductor cooling device and an air conditioner cooling evaporator, respectively, 39 indicates a transmitting pipe, 38 indicates fins and 40 indicates heat isolation materials.

Prior art external counterpulsation apparatus utilized materials such as vinyl, leather, cloth or canvas to make the balloon cuffs. These cuffs are wrapped tightly around the lower limbs with balloons put in between the cuffs and the body. When compressed gas is inflated into the balloons, the cuff will also expand and extend outward due to the elasticity and extensibility of its material, causing significant energy loss since a large portion of the compressed air serves to deform the cuff. More importantly, when compressed air is used to expand and extend the cuffs outwardly, the pressure inside the balloons will not be built up quickly, reducing the rate of compression of the tissue mass and the underlying vasculature, causing a slower external counterpulsation pulse wave moving up the aorta. This reduces the effectiveness of counterpulsation in increasing the perfusion pressure to the coronary arteries and, therefore, the development of collateral circulations (i.e., a set of new vessels formed in the myocardium (heart) bypassing the blockages in the coronary arteries). Therefore, the present invention provides the use of rigid or semi-rigid materials with little or no extensibility and elasticity so that the introduction of compressed air into the balloons will not cause the deformation or expansion of the cuffs, thereby requiring less pressurized air and reducing energy loss. Furthermore, the use of rigid or semi-rigid materials in making the cuffs will result in rapid filling of the balloons, quicker compression of the surrounded tissue mass and, therefore, a steeper external counterpulsation leading pulse wave traveling retrogradedly up the aorta to the heart.

FIG. 6 is a schematic diagram of the balloon device 41 in the external counterpulsation apparatus according to the present invention. A balloon cuff body 44 surrounding the balloon 25 (not shown) is made of materials of certain toughness and hardness such as plastic (e.g., polyacrylate), aluminum, or other metallic plates, rather than of leather, cloth and canvas, thereby substantially reducing the inflatability and extendibility of the balloon cuff body. Tubular balloon cuff bodies can be fabricated to fit the upper limbs, lower limbs, and other balloon cuff bodies can be fabricated to fit the buttocks, such that the balloon cuff body tightly surrounds the body without gaps, and is prevented from slipping. Different sizes of balloon cuff bodies should be provided to meet the requirements of different body shapes. The balloon cuff body 44 can be prefabricated or pre-formed or formed out of thermally changeable materials in whatever form is necessary. There are materials of plastic form which become flexible and can be molded into different shape when heated to a temperature of 50 to 60° C., and will become rigid and non-distensible when the temperature is lower, generally to room temperature, 20 to 30° C. Such materials are available commercially in the United States, such as the Orthoplast used in orthopaedics.

Generally, any space that exists between the cuff and the surrounded body except that occupied by the balloon is known as dead space. It is essential to reduce this dead space as much as possible so that the least amount of energy in the form of compressed air is required to inflate the balloons to the required pressure in the quickest way. This will reduce the size and energy consumption of the compressor, reduce noise level, and therefore reduce the total size of the external counterpulsation apparatus.

To achieve the object of closely fitting the body and reducing the dead space, proper paddings 43 can be provided between the balloons and the balloon cuffs. The paddings may be bags of unformed materials (such as water, powder, fine sand, etc.) or triangular pads made of formed materials (e.g., rubber), the former could form a pressure bearing surface which fits the contour of the pressure bearing portion of the body when it bears pressure; while the latter could meet the needs of patients of various bodily forms by simply moving the paddings upward or downward to avoid the need to provide balloon cuffs of various sizes. To prevent the skin of a patient from being chaffed, a result of vibrations produced during counterpulsation, the edges of the balloon cuff body should be smoothed. This could be done by slightly turning the edges outwardly, and also could be done by wrapping the edges with soft materials (e.g. cloth, sponge, etc.). The balloon cuff body could be made from a single piece of material, but for convenient operation, it is preferable that it be fabricated in separated pieces which are coupled together with hinges 42 to enable freely opening and closing.

A balloon cuff body of proper size is selected or fitting paddings are inserted into the balloon cuff to fit the bodily form of the patient to make the balloon cuff closely encircle the corresponding portion of the patient. Fixing belts 45 are then tightened, and counterpulsation can begin.

FIG. 7 is a flow chart of the control method of the external counterpulsation apparatus according to the present invention, which comprises the steps of: a). obtaining an impedance cardiograph and electrocardiographic signals having a clear and stable wave form in the counterpulsation state by the use of detector electrodes 1, high frequency constant current source 2, and electrocardiographic and impedance signal amplifier-filter means 3, 4 and 5, which are collected and displayed by the computer system 7 (101); b). the computer system detecting the QRS wave of the electrocardiograph signal (102), performing adaptive processing of the impedance blood flow signal (103), obtaining the starting point of the counterpulsation blood flow wave by detecting the impedance cardiograph after self adaptive filtering processing (104), and calculating the data for controlling the inflation and deflation time of the counterpulsation apparatus from the interval of the R wave of the electrocardiographic signal and the starting point of the counterpulsing blood flow wave (105); c). obtaining an objective index reflecting the curative effect of counterpulsation by detecting the peak amplitude of the waveform and duration of the heart systolic wave and counterpulsing wave in the impedance cardiograph (106); and d). controlling the inflation and deflation of the external counterpulsation apparatus by the computer (107). For the safety of the patient during counterpulsation, the control method of the present invention further comprises the following steps: e). detecting the blood pressure state of the patient with a blood pressure detector means during counterpulsation (108); and f). detecting the oxygen saturation of the blood of the patient with a blood oxygen detector during counterpulsation (109). If they detected blood pressure value exceeds a predetermined value, or the blood oxygen saturation goes below a predetermined value, then the computer will direct the apparatus to stop counterpulsation.

In general, the only serious complications from external counterpulsation treatment are pulmonary edema and cerebral hemorrhage. Pulmonary edema may arise because of left ventricular (left heart) failure, and usually can be detected with a rapid drop in the oxygen saturation of the arterial blood, from a normal value of 95–98% to a value lower than 85–90%. The monitor of oxygen saturation is an extremely sensitive parameter for the detection of pulmonary congestion due to left heart failure. The oxygen saturation can be monitored with a pulse oximeter available commercially and commonly used in any operating room. The use of pulse oximetry as a noninvasive method to detect the complications of pulmonary congestion (edema) as well as left heart failure is a novel concept provided in the present invention. Furthermore, cerebral hemorrhage usually result from high arterial blood pressure (hypertension). Since an effective external counterpulsation can raise the peak diastolic pressure to 40 to 60 mm Hg above systolic blood pressure, it is important not only to measure the resting blood pressure of the patient before initiation of external counterpulsation (so that hypertension patients can be treated medically to reduce their blood pressure before counterpulsation treatment), but it is also important to monitor the peak arterial blood pressure during treatment to ensure the peak blood pressure will not rise more than 40 to 50 mm Hg above resting systolic pressure. The present invention provides a novel means to monitor the peak blood pressure effectively. Historically, it has been extremely difficult to measure blood pressure using any of the presently available measuring methods during external counterpulsation because of motion artifact as well as the noisy environment. The present invention provides a means to accurately determine the peak blood pressure, thereby producing a critical parameter in eliminating such dangerous complications as cerebral hemorrhage.

A closed loop control procedure is performed by the computer and is as follows: At the beginning of the counterpulsation, the computer automatically sets the balloon inflation time to be at the end of the T wave of the electrocardiograph. Due to the delay before the arrival of the counterpulsing wave at the aorta, the closing point of the aortic valve and the starting point of the counterpulsation wave can be detected from the heart impedance blood flow graph by the computer. The computer adjusts the inflation time of the counterpulsation apparatus according to the time difference between these two points to move the starting point of the counterpulsing wave gradually towards the closing point of the aorta. While gradually matching these two points, the computer also calculates the aorta closing time with the Bazett formula ($T_{QT}=K\sqrt{T_{RR}}$) because of the effect of counterpulsation on the automatic detecting of the closing point of the aorta. The time QT calculated with the Bazett formula is taken as the closing time of the aortic valve after the Q wave of the electrocardiograph has been detected. This makes the starting point of the counterpulsing wave fall into a range centered at the closing time of the aortic valve. In the procedure of gradually matching the two points, the detection of the starting point of the counterpulsing wave may be affected by blood expulsion from the heart and the variation of blood flow inside the chest. If so, the computer determines the time delay between the arrival of the counterpulsing wave at the central region of the aorta and its formation by a the pressurization of the lower limbs of the patient, by determining the time difference between the detected starting point of the counterpulsing wave and the inflation time. The computer adjusts the counterpulsation inflation time, such that the starting point of the counterpulsation formed after the time delay falls into a range centered at the closing time of the aortic valve. The computer keeps it in this range during counterpulsation, thereby performing loop control.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An external counterpulsation apparatus for use with a patient, comprising:
    a plurality of inflatable members adapted to be received about a limb of the patient;
    a source of compressed fluid in fluid communication with said plurality of inflatable members;
    a fluid distribution device connected to said inflatable members and operable to distribute compressed fluid from said source of compressed fluid to said inflatable members;
    a high-frequency current source operably applied to the patient to produce an electrocardiographic signal and a blood flow impedance signal;
    an amplifier-filter circuit operably conditioning said electrocardiographic signal received from the patient;
    a heart impedance signal amplifier operably receiving said blood flow impedance signal from the patient; and
    a computer operably processing said electrocardiographic signal and said blood flow impedance signal and operably associated with the fluid distribution device for controlling distribution of compressed fluid to said plurality of inflatable members based on said processed electrocardiographic signal and blood flow impedance signal.

2. The external counterpulsation apparatus of claim 1, wherein said amplifier-filter circuit includes a low-pass differential amplifier and a band-pass filter for amplifying and filtering said electrocardiographic signal received from the patient.

3. The external counterpulsation apparatus of claim 1, wherein said computer detects a QRS wave from said electrocardiographic signal.

4. The external counterpulsation apparatus of claim 1, wherein said computer performs adaptive processing of said impedance blood flow signal.

5. The external counterpulsation apparatus of claim 4, wherein said computer uses an impedance reference signal to adaptively process said impedance blood flow signal.

6. The external counterpulsation apparatus of claim 1, wherein said computer determines electrocardiographic characteristic points from a group comprising: aortic valve closure, diastolic amplitude and systolic amplitude.

7. The external counterpulsation apparatus of claim 1, further comprising a drive circuit electrically controlled by said computer to inflate and deflate said plurality of inflatable members.

8. The external counterpulsation apparatus of claim 1, further comprising a pulse transducer electrically connected to said computer and operably detecting a pulse wave.

9. The external counterpulsation apparatus of claim 8, further comprising a pressure transducer electrically connected to said computer for detecting a maximum arterial pressure.

10. The external counterpulsation apparatus of claim 9, wherein said computer processes said pressure and pulse signals.

11. The external counterpulsation apparatus of claim 10, wherein said computer controls counterpulsation based on said processed pressure and pulse signals.

12. The external counterpulsation apparatus of claim 10, wherein said computer calculates oxygen saturation based on said processed pressure and pulse signals.

* * * * *